United States Patent [19]

Hasegawa et al.

[11] Patent Number: 5,106,859
[45] Date of Patent: Apr. 21, 1992

[54] CERTAIN 1,3,4-THIADIAZOLE DERIVATIVES AND ANTI-ULCER AGENT COMPRISING SAID DERIVATIVES AS ACTIVE INGREDIENT

[75] Inventors: Yoshihiro Hasegawa; Toshihiko Yanagisawa; Kunio Hosaka; Hiroshi Mitsuhashi, all of Ibaraki, Japan

[73] Assignee: Tsumura & Co., Tokyo, Japan

[21] Appl. No.: 613,693

[22] PCT Filed: Sep. 29, 1989

[86] PCT No.: PCT/JP89/00989
§ 371 Date: Jul. 30, 1990
§ 102(e) Date: Jul. 30, 1990

[87] PCT Pub. No.: WO90/03377
PCT Pub. Date: Apr. 5, 1990

[30] Foreign Application Priority Data

Sep. 30, 1988 [JP] Japan .................. 63-243899

[51] Int. Cl.$^5$ .................. C07D 401/14; A61K 31/44
[52] U.S. Cl. .................. 514/333; 546/256; 546/277
[58] Field of Search ............ 514/333; 546/277, 256

[56] References Cited

PUBLICATIONS

Ash et al., "2-Pyridine Aldoximes", *Chemical Abstracts*, vol. 72, No. 23, Abstract No. 121377y (Jun. 8, 1970), p. 337.

Kubota et al., "Synthesis of 1,3,4-Thiadiazole Derivatives. II. Synthesis of 1,3,4-Thiadiazoline-5-Thiones from Amidrazones and Carbon Disulfide", *Chemical Abstracts*, vol. 73, No. 19, Abstract No. 988/w (Nov. 9, 1970), p. 369.

Chemical Abstracts, vol. 112, No. 5, Jan. 29, 1990.
Chemical Abstracts, vol. 112, No. 17, Apr. 23, 1990.

*Primary Examiner*—Alan L. Rotman
*Attorney, Agent, or Firm*—Burns, Doane, Swecker & Mathis

[57] ABSTRACT

A novel thiadiazole derivative represented by the following formula I:

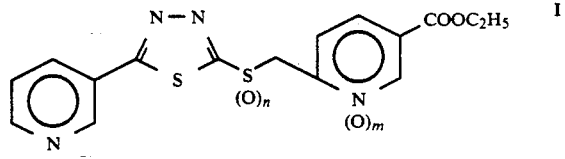

wherein when n is 0, m is 0, and when n is 1, m is 0 or 1, and the preparation of this derivative and the use of this derivative as an anti-ulcer agent.

5 Claims, No Drawings

CERTAIN 1,3,4-THIADIAZOLE DERIVATIVES AND ANTI-ULCER AGENT COMPRISING SAID DERIVATIVES AS ACTIVE INGREDIENT

TECHNICAL FIELD

The present invention relates to a novel 1,3,4-thiadiazole derivative and an anti-ulcer agent comprising this derivative as the active ingredient.

BACKGROUND ART

Recently, the number of patients suffering from digestive ulcers has increased and the development of an antacid, an anticholinergic agent, a histamine $H_2$ receptor antagonist and the like has been promoted for the remedy of these ulcers. These agents, however, are not ideal medicines for a radical cure of these ulcers, and accordingly, the development of an agent having a greater anti-ulcer action is desired.

DISCLOSURE OF THE INVENTION

With a view to finding a substance having a better anti-ulcer action, the inventors synthesized many novel compounds and carried out screening, and as a result, found that effective compounds are present among 1,3,4-thiadiazole derivatives. We carried out further research based on this finding, and thus completed the present invention.

More specifically, in accordance with the present invention, there are provided a thiadiazole derivative represented by the following formula I, and an anti-ulcer agent comprising this derivative (hereinafter referred to as "compound of formula I") as the active ingredient:

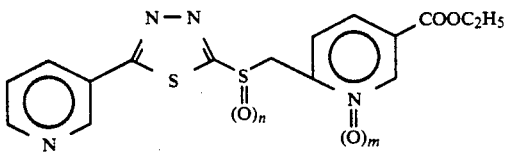

wherein when n is 0, m is 0, and when n is 1, m is 0 or 1.

BEST MODE OF CARRYING OUT THE INVENTION

The compound of formula I can be obtained, for example, by using 2-(3-pyridyl)-1,3,4-thiadiazoline-5-thione represented by the following formula II (hereinafter referred to as the "compound of formula II") as the starting compound and reacting this compound with ethyl 6-chloromethylnicotinate represented by the following formula III (hereinafter referred to as the "compound of formula III") to effect thioetherification:

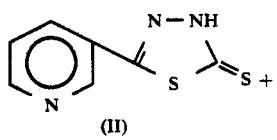

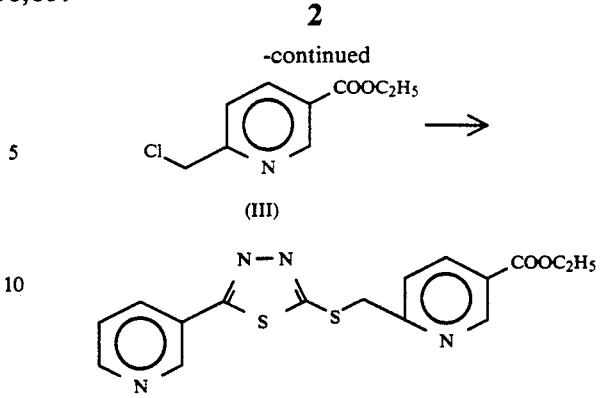

The above reaction is particularly carried out in the presence of a base, and as specific examples of the base, there can be mentioned sodium hydroxide, sodium carbonate, potassium carbonate and potassium hydroxide. As the solvent, mixed solvents of water with a water-insoluble solvent such as benzene, chloroform, methylene chloride or toluene, and alcohols such as methanol and ethanol are preferably used.

The reaction time is preferably about 1 to about 30 hours. The reaction is sufficiently advanced at room temperature, but the reaction can be conducted under heating according to need.

After termination of the reaction, the reaction product can be purified by a customary purification process, for example, a recrystallization process using an appropriate solvent (such as methanol, ethanol or acetonitrile).

The obtained compound can be converted to an oxide by addition of a peroxide.

As specific examples of the peroxide, m-chloroperbenzoic acid, perbenzoic acid and sodium periodate can be used, and the reaction is completed within 15 minutes to 6 hours at $-20°$ to $40°$ C. in an organic solvent such as chloroform or methylene chloride (if the starting compound is not dissolved, an alcohol, acetic acid or water can be appropriately used). After termination of the reaction, the reaction product can be purified by the above-mentioned process.

Furthermore, an oxide can be formed by using oxone, which is a composite of $2-KHSO_5$, $KHSO_4$ and $K_2SO_4$. In this case, the reaction is preferably carried out in the presence of an acid.

As specific examples of the solvent, there can be mentioned acetic acid/water, sulfuric acid/water, nitric acid/water and methanol/water. An acid such as methane-sulfonic acid can be added according to need. The reaction is completed with 15 minutes to 6 hours, and the reaction temperature is preferably $-20°$ C. to room temperature. After termination of the reaction, the reaction mixture is neutralized with an alkali and extracted with an organic solvent such as dichloromethane or chloroform, and the reaction product can be purified by a usual purification process (for example, by a recrystallization process or a column chromatography process using silica gel or the like).

The compounds of formula II and III, which are the starting compounds for the preparation of the compound of formula I, are commercially available or can be prepared from commercially available compounds. Accordingly, the industrial working of the present invention involves no problems.

The compound of formula II can be prepared by using a nitrile as the starting compound, reacting the nitrile with hydrazine to form an amidorazone compound and cyclizing the compound with carbon disulfide [Chem. Pharm. Bull., 18 (8), 1696 (1970)].

The compound of formula III can be prepared, for example, by converting ethyl 6-methylnicotinate to an N-oxide, rearranging the N-oxide with acetic anhydride to effect ethanolysis, and reacting the obtained ethyl 6-hydroxymethylnicotinate with thionyl chloride [J. Chem. Soc., 1841 (1963)].

Specific examples of the preparation of the compounds of formulae II and III will now be described.

SPECIFIC EXAMPLE 1

Preparation of 2-(3-pyridy)-1,3,4-thiadiazoline 5-thione

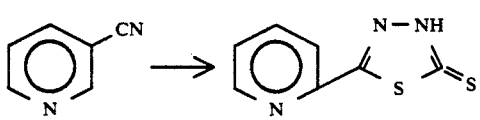

A mixture of 12.4 g of 3-pyridine carbonitrile, 57 ml of hydrazine monohydrate and 40 ml of methanol was allowed to stand at room temperature for 4 days. The solvent was removed under a reduced pressure, 200 ml of ethanol and 14 ml of carbon disulfide were added to the obtained residue, and the mixture was stirred at room temperature for 2.5 hours. The precipitated crystal was recovered by filtration, washed with ethanol, and dried to obtain 21.0 g of 2-(3-pyridy)-1,3,4-thiadiazoline-5-thione.

SPECIFIC EXAMPLE 2

Preparation of ethyl 6-hydroxymethylnicotinate

① 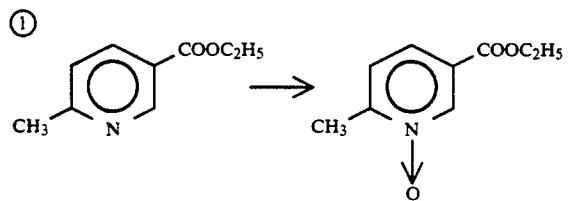

A mixture of 14.9 g of ethyl 6-methylnicotinate, 60 ml of acetic acid and 21.5 ml of 30% hydrogen peroxide was stirred at 80° C. for 16 hours, the reaction liquid was concentrated under a reduced pressure, water was added to the concentrate, and the mixture was extracted with chloroform. The chloroform layer was washed with an aqueous solution of potassium carbonate and dried over anhydrous potassium carbonate, and the solvent was removed under a reduced pressure to obtain 14.0 g of 5-ethoxycarbonyl-2-methyl pyridine-1-oxide.

② 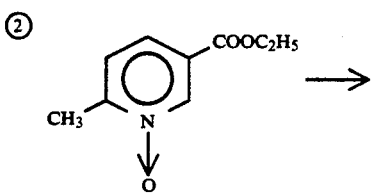

-continued

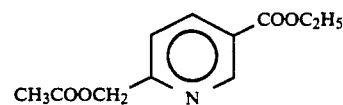

A mixture of 13.7 g of 5-ethoxycarbonyl-2-methyl-pyridine-1-oxide and 15 g of acetic anhydride was stirred under reflux. Excess acetic anhydride was removed under a reduced pressure, and the residue was purified by distillation under a reduced pressure (110° C./0.1 mmHg) to obtain 10.0 g of ethyl 6-acetoxymethylnicotinate.

③ 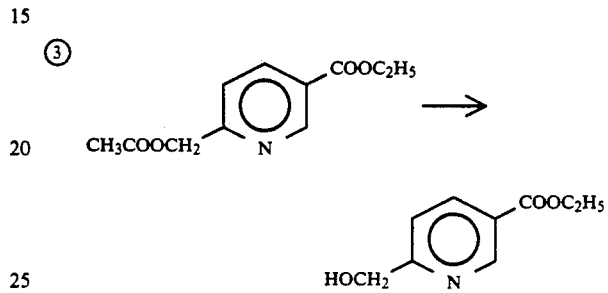

To a solution of 9.2 g of ethyl 6-acetoxymethylnicotinate in chloroform (40 ml) was added an ethanol solution of sodium ethoxide prepared from 0.92 g of sodium and 23 ml of ethanol, and the mixture was stirred at room temperature for 2 hours. The reaction liquid was poured into water containing 6 ml of acetic acid and the chloroform layer was separated and dried with anhydrous sodium sulfate. The solvent was removed under reduced pressure, carbon tetrachloride was added to the residue, and the insoluble substance was removed by filtration. The filtrate was concentrated under reduced pressure and the residue was recrystallized from ethyl acetate/hexane to obtain 5.1 g of ethyl 6-hydroxymethylnicotinate.

④ 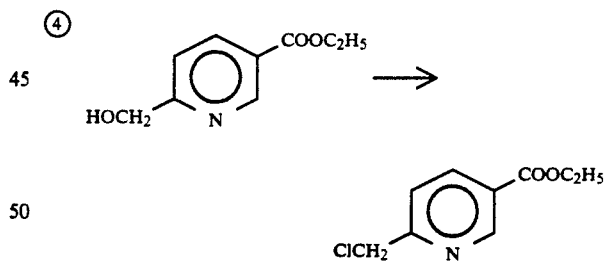

A solution of 10.5 g of ethyl 6-hydroxymethylnicotinate in chloroform (100 ml) was cooled to 0° C., and 8.28 g of thionyl chloride was added dropwise to the solution. The mixture was stirred at 0° C. for 2 hours, an aqueous solution of sodium hydrogencarbonate was added, and the mixture was extracted with dichloromethane. The organic layer was washed with a saturated aqueous solution of sodium chloride, dried over anhydrous sodium sulfate, the solvent was removed under reduced pressure, and the residue was purified by silica gel column chromatography (n-hexene/ethyl acetate=6/1) to obtain 10.52 g of ethyl 6-chloromethylnicotinate.

With reference to the following tests, it will now be demonstrated that the compound of formula I has a superior anti-ulcer activity and is valuable as an anti-ulcer agent.

TEST EXAMPLE 1

To male rats of the Wistar strain (each group consisting of 8 rats) having a body weight of 160 to 180 g, which had been fasted for 24 hours, was orally administered 3 mg/kg of the compound of formula I in the form of a suspension in a 0.5% solution of carboxymethyl cellulose (CMC), and after 30 minutes, 1 ml/200 of 150 M hydrochloric acid/60% ethanol was orally administered to the rats. One hour after the administration of the hydrochloric acid/ethanol, the rats were subjected to laparotomy, and the length of the damaged part formed on the mucosa of the stomach was compared, as the mucosa damage coefficient, with that in the control group. Only the 0.5% solution of CMC not containing the compound of formula I was orally administered to the control group. The inhibition ratio was calculated according to the following formula:

$$\text{Inhibition ratio (\%)} = \frac{A - B}{A} \times 100$$

wherein A represents the value of the control group and B represents the value of the group to which the compound of formula I was administered. The results are shown in Table 1.

TABLE 1

| Results of Anti-Ulcer Test by Oral Administration | |
|---|---|
| Compound Tested | Inhibition Ratio (%) |
| compound obtained in Example 1 | 42.9 |
| compound obtained in Example 2 | 91.5 |

From the foregoing results, it was confirmed that the compound of formula I has an inhibiting and curing effect on ulcers.

When the compound of formula I was orally administered to mice of the ddY line (each group consisting of 7 rats), no fatalities occurred at a dose of up 3500 mg/kg, and therefore, it was confirmed that the compound of formula I has a low acute toxicity and is safe.

Namely, the compound of formula I is valuable as an anti-ulcer agent.

The dose and formulation of the compound of formula I will now be described. The compound of formula I can be administered to animals and men alone or together with a pharmaceutical carrier. The administration form is not particularly critical, and an appropriate form can be selected according to need. For example, there can be mentioned agents for oral administration, such as a tablet, a capsule, a granule, a fine granule, and a powder, and agents for external application, such as an injection and a suppository.

For the compound of formula I to exert an intended effect, preferably the compound of formula I is administered at a daily dose of 50 mg to 2 g based on the weight of the compound of formula I for an adult several times a day, although the appropriate dose differs according to the age and body weight of a patient and the degree of the disease.

An agent for oral administration can be prepared by customary procedures by using, for example, starch, lacrose, refined sugar, mannitol, carboxymethyl cellulose, corn starch, an inorganic salt or the like.

For the formulation of this type of agent, a binder, a disintegrating agent, a surface active agent, a lubricant, a flowability improver, a taste improver, a colorant, and a perfume can be used in addition to the above-mentioned excipient. Specific examples of these adjuvants are described below.

(Binder)

Starch, dextrin, gum arabic powder, gelatin, hydroxypropyl starch, methyl cellulose, sodium carboxymethyl cellulose, hydroxypropyl cellulose, crystalline cellulose, ethyl cellulose, polyvinyl pyrrolidone and Macrogol.

(Disintegrating Agent)

Starch, hydroxypropyl starch, sodium carboxymethyl cellulose, calcium carboxymethyl cellulose, carboxymethyl cellulose and lowly substituted hydroxypropyl cellulose.

(Surface Active Agent)

Sodium lauryl sulfate, soybean lecithin, sucrose fatty acid ester and Polysorbate 80.

(Lubricant)

Talc, waxes, hydrogenated vegetable oils, sucrose fatty acid ester, magnesium stearate, calcium stearate, aluminum stearate and polyethylene glycol.

(Flowability Improver)

Light silicic anhydride, dry aluminum hydroxide gel, synthetic aluminum silicate and magnesium silicate.

The compound of formula I can be administered in the form of a suspension, an emulsion, a syrup or an elixir agent. These preparations can contain a taste or smell improver and a colorant.

For the non-oral agent to exert an intended effect, preferably the non-oral agent is administered in an amount of 0.1 to 500 mg/day as the compound of formula I for an adult by intravenous injection, intravenous drip, hyperdemic injection or intramuscular injection, although the preferred administered amount differs according to the age and body weight of a patient and the degree of the disease.

The non-oral agent can be prepared by customary procedures. As the diluent, there are generally used distilled water for injection, a physiological saline solution, an aqueous solution of glucose, a vegetable oil for injection, sesame oil, peanut oil, soybean oil, corn oil, propylene glycol and polyethylene glycol. In view of the stability, there can be adopted a method in which the non-oral agent is filled in a vial or the like and frozen, water is removed by a usual freeze-drying technique, and the liquid is formed again from the freeze-dried product just before application. An isotonic agent, a stabilizer, an antiseptic agent and an analgesic agent can be added to the non-oral agent.

Coating agents such as an external lotion and an ointment, and a suppository for intrarectal administration can be mentioned as another non-oral agent, and can be prepared by customary procedures.

The present invention will now be described in detail with reference to the following examples, that by no means limit the scope of the invention.

EXAMPLE 1

2-[(5-Ethoxycarbonylpyridin-2-yl)methylthio]-5-(3-pyridyl)-1,3,4-thiadiazole of the following formula

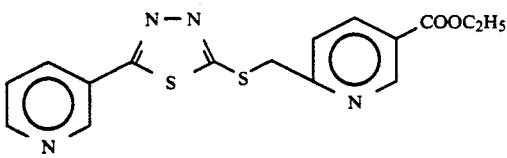

A mixture of 11.28 g of 2-(3-pyridyl)-1,3,4-thiadiazoline-5-thione obtained in Specific Example 1, 10.50 g of ethyl 6-chloromethylnicotinate obtained in Specific Example 2, 15.70 g of potassium carbonate and 200 ml of ethanol was stirred at 50° C. for 3 hours, and the reaction mixture was poured into water at room temperature. The precipitated crystal was recovered by filtration, washed with water, and recrystallized from ethanol to obtain 18.07 g of 2-[(5-ethoxycarbonylpyridin-2-yl)methylthio]-5-(3-pyridyl)-1,3,4-thiadiazole.

Molecular formula: $C_{16}H_{14}N_4O_2S_2$ (358.44)
Melting point: 147° to 148° C.
Mass spectrum, EI-MS: 358 (M+), 325, 313, 297, 254
Infrared absorption spectrum, max/KBr cm$^{-1}$: 1712, 1598, 1364, 1290, 1268
Proton-nuclear magnetic resonance spectrum (δ ppm in CDCl$_3$): 9.18 (1H, br d, J=2 Hz), 9.05 (1H, dd, J=2, 0.7 Hz), 8.71 (1H, dd, J=5, 1.7 Hz), 8.27 (1H, dd, J=8, 2 Hz), 8.22 (1H, ddd, J=8, 2, 1.7 Hz), 7.65 (1H, br d, J=8 Hz), 7.42 (1H, ddd, J=8, 5, 0.5 Hz), 4.80 (2H, s), 4.41 (2H, q, J=7.1 Hz), 1.40 (3H, t, J=7.1 Hz)

EXAMPLE 2

2-[(5-Ethoxycarbonylpyridin-2-yl)methylsulfinyl]-5-(3-pyridyl)-1,3,4-thiadiazole of the following formula

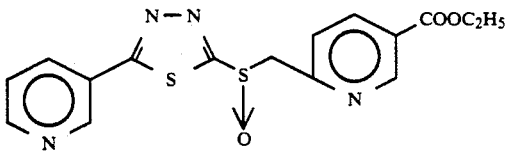

A mixed solution of 4.92 g of 2-[(5-ethoxycarbonylpyridin-2-yl)methylthio]-5-(3-pyridyl)-1,3,4-thiadiazole, 2.7 ml of methane-sulfonic acid, 18 ml of acetic acid, and 45 ml of water was cooled to 0° C., oxone (4.65 g) was added to the solution, and the mixture was stirred for 3 hours. The reaction mixture was neutralized with an aqueous solution of sodium hydrogencarbonate so that the pH value was 5, and the mixture was extracted with dichloromethane. The organic layer was washed with a saturated aqueous solution of sodium chloride and dried over anhydrous sodium sulfate. The solvent was removed under reduced pressure, the residue was separated and purified by silica gel column chromatography (chloroform/methanol=30/1), and a fraction having an Rf value of 0.25 was recrystallized from ethanol to obtain 2.45 g of 2-[(5-ethoxycarbonylpyridin-2-yl)methylsulfinyl]-5-(3-pyridyl)-1,3,4-thiadiazole.

Molecular weight: $C_{16}H_{14}N_4O_3S_2$ (374.44)
Melting point: 126° to 128° C.
Elementary analysis:
Calculated values: C=51.32, H=3.77, N=14.96
Found values: C=51.29, H=3.51, N=14.89

Mass spectrum, EI-MS: 374 (M+), 222, 195, 164
Infrared absorption spectrum, max/KBr cm$^{-1}$: 1726, 1308, 1288, 1118, 1038
Proton-nuclear magnetic resonance spectrum (δ ppm in CDCl$_3$): 9.15 (2H, m), 8.79 (1H, dd, J=5, 1.8 Hz), 8.32 (2H, m), 7.50 (1H, dd, J=8, 5 Hz), 7.42 (1H, d, J=8.1 Hz), 4.85 (1H, d, J=12.9 Hz), 4.70 (1H, d, J=12.9 Hz), 4.42 (2H, q, J=7.1 Hz), 1.41 (3H, t, J=7.1 Hz)

EXAMPLE 3

2-[(1-oxy-5-ethoxycarbonylpyridin-2-yl)methyl-sulfinyl]-5-(3-pyridyl)-1,3,4-thiadiazole of the following formula

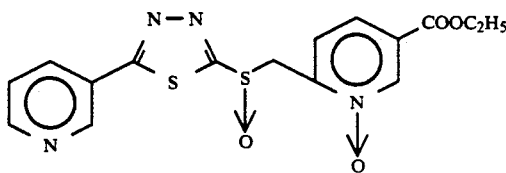

The fraction having an Rf value of 0.20, obtained by silica gel column chromatography (chloroform/methanol=30/1) in Example 2, was recrystallized from ethanol to obtain 100 mg of 2-[(1-oxy-5-ethoxycarbonylpyridin-2-yl)methylsulfinyl]-5-(3-pyridyl)-1,3,4-thiadiazole.

Molecular formula: $C_{16}H_{14}N_4O_4S_2$ (390.44)
Melting point: 130° to 132° C. (decomposition)
Mass spectrum, EI-MS: 374 (M+ −16), 358, 195, 163
Infrared absorption spectrum, max/KBr cm$^{-1}$: 1726, 1408, 1306, 1238, 1068
Proton-nuclear magnetic resonance spectrum (δ ppm in CDCl$_3$): 9.18 (1H, br d), 8.87 (1H, d, J=1.5 Hz), 8.80 (1H, dd, J=5, 1.5 Hz), 8.35 (1H, dt, J=8, 1.5 Hz), 7.87 (1H, dd, J=8, 1.5 Hz), 7.51 (2H, m), 5.09 (1H, d, J=12.2 Hz), 4.78 (1H, d, J=12.2 Hz), 4.44 (2H, q, J=7 Hz), 1.42 (3H, t, J=7 Hz)

EXAMPLE 4

| (1) | Corn starch | 44 g |
|---|---|---|
| (2) | Crystalline cellulose | 40 g |
| (3) | Calcium carboxymethyl cellulose | 5 g |
| (4) | Light silicic anhydride | 0.5 g |
| (5) | Magnesium stearate | 0.5 g |
| (6) | Compound prepared in Example 1 | 10 g |
| | Total | 100 g |

According to the above-mentioned recipe, ingredients (1) through (6) were homogeneously mixed, and the mixture was compression-molded by a tableting machine to obtain tablets each having a weight of 200 mg.

Each tablet contained 20 mg of the compound, and 5 to 20 tablets per day were separately administered to an adult several times in one day.

EXAMPLE 5

| (1) | Crystalline cellulose | 84.5 g |
|---|---|---|
| (2) | Magnesium stearate | 0.5 g |
| (3) | Calcium carboxymethyl cellulose | 5 g |
| (4) | Compound obtained in Example 2 | 10 g |
| | Total | 100 g |

According to the above-mentioned recipe, ingredients (1) and (4) and a part of ingredient (2) were homogeneously mixed and the mixture was compression-molded, and the compression-molded product was mixed with ingredient (3) and the remainder of ingredient (2), and the mixture was compression-molded by a tableting machine to obtain tablets each having a weight of 200 mg.

Each tablet contained 20 mg of the compound, and 5 to 20 tablets per day were separately administered several times in one day.

EXAMPLE 6

| (1) | Crystalline cellulose | 49.5 g |
|---|---|---|
| (2) | 10% Solution of hydroxypropyl cellulose in ethanol | 35 g |
| (3) | Calcium carboxymethyl cellulose | 5 g |
| (4) | Magnesium stearate | 0.5 g |
| (5) | Compound obtained in Example 1 | 10 g |
| | Total | 100 g |

According to the above-mentioned recipe, ingredients (1), (2) and (5) were homogeneously mixed, and the mixture was kneaded according to customary procedures, granulated by an extrusion granulator, dried, and disintegrated. Then, the disintegration product was mixed with ingredients (3) and (4), and the mixture was compression-molded by a tableting machine to form tablets each having a weight of 200 mg.

Each of the tablets contained 20 mg of the compound, and 5 to 20 tablets were separately administered to an adult several times in one day.

EXAMPLE 7

| (1) | Corn starch | 84 g |
|---|---|---|
| (2) | Magnesium stearate | 0.5 g |
| (3) | Calcium carboxymethyl cellulose | 5 g |
| (4) | Light silicic anhydride | 0.5 g |
| (5) | Compound obtained in Example 3 | 10 g |
| | Total | 100 g |

According to the above-mentioned recipe, ingredients (1) through (5) were homogeneously mixed, and the mixture was compression-molded by a compression molding machine, pulverized by a pulverizer, and classified to obtain a granule.

The obtained granule contained 100 mg of the compound per gram, and 1 to 10 g of the granule was separately administered to an adult several times in one day.

EXAMPLE 8

| (1) | Crystalline cellulose | 55 g |
|---|---|---|
| (2) | 10% Solution of hydroxypropyl cellulose in ethanol | 35 g |
| (3) | Compound obtained in Example 1 | 10 g |
| | Total | 100 g |

According to the above-mentioned recipe, ingredients (1) through (3) were homogeneously mixed and kneaded, and the mixture was granulated by an extrusion granulator, dried, and classified to obtain a granule.

The granule contained 100 mg of the compound per gram and 1 to 4 g of the granule was separately administered to an adult several times in one day.

EXAMPLE 9

| (1) | Corn starch | 89.5 g |
|---|---|---|
| (2) | Light silicic anhydride | 0.5 g |
| (3) | Compound obtained in Example 2 | 10 g |
| | Total | 100 g |

According to the above-mentioned recipe, ingredients (1) through (3) were homogeneously mixed, and 200 mg of the mixture was filled in capsules No. 2.

Each capsule contained 20 mg of the compound, and 5 to 20 capsules were separately administered to an adult several times in one day.

EXAMPLE 10

| (1) | Distilled water for injection | 89.5 g |
|---|---|---|
| (2) | Soybean oil | 5 g |
| (3) | Soybean lipid | 2.5 g |
| (4) | Glycerol | 2 g |
| (5) | Compound obtained in Example 1 | 1 g |
| | Total | 100 g |

According to the above-mentioned recipe, ingredient (5) was dissolved in (2) and (3) and a solution of (1) and (4) were added to the obtained solution to effect emulsification and obtain an injection.

We claim:

1. A thiadiazole compound represented by the following formula I:

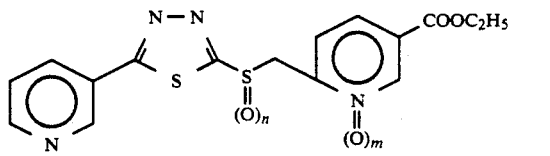

wherein n is 0, m is 0, and when n is 1, m is 0 or 1.

2. A compound as set forth in claim 1, which is selected from the group consisting of 2-[(5-ethoxycarbonylpyridin-2-yl)methylthio]-5-(3-pyridyl)-1,3,4-thiadiazole, 2-[(5-ethoxycarbonylpyridin-2-yl)methylsulfinyl]-5-(3-pyridyl)-1,3,4-thiadiazole and 2-[(1-oxy-5-ethoxycarbonylpyridin-2-yl)methylsulfinyl]-5-(3-pyridyl)-1,3,4-thiadiazole.

3. An anti-ulcer composition as set forth in claim 2, wherein the thiadiazole derivative is selected from the group consisting of 2-[(5-ethoxycarbonylpyridin-2-yl)methylthio]-5-(3-pyridyl)-1,3,4-thiadiazole, 2-[(5-ethoxycarbonylpyridin-2-yl)methylsulfinyl]-5-(3-pyridyl)-1,3,4-thiadiazole and 2-[(1-oxy-5-ethoxycarbonylpyridin-2-yl)methylsulfinyl]-5-(3-pyridyl)-1,3,4-thiadiazole.

4. An anti-ulcer composition which comprises as the effect amount of active ingredient a thiadiazole derivative represented by the following formula:

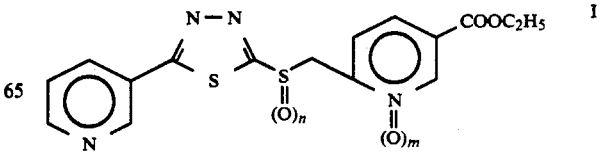

wherein when n is 0, m is 0, and when n is 1, m is 0 or 1 in admixture with an inert carrier.

5. A method of treating an ulcer, which comprises administering to a patient in need of such treatment an effective amount of a thiadiazole derivative represented by the following formula:

wherein when n is 0, m is 0, and n is 1, m is 0 or 1.

* * * * *